United States Patent [19]

Noda

[11] Patent Number: 5,211,650
[45] Date of Patent: May 18, 1993

[54] DUAL FUNCTION SUTURING DEVICE AND METHOD

[75] Inventor: Wayne A. Noda, Mission Vieio, Calif.

[73] Assignee: LaParomed Corporation, Irvine, Calif.

[21] Appl. No.: 912,353

[22] Filed: Jul. 13, 1992

Related U.S. Application Data

[63] Continuation-in-part of Ser. No. 638,887, Jan. 7, 1991, Pat. No. 5,129,912.

[51] Int. Cl.⁵ ............................................. A61B 17/00
[52] U.S. Cl. ...................................... 606/139; 606/147; 606/148; 289/1.2; 289/1.5; 289/17; 604/167; 604/256
[58] Field of Search ............. 606/139, 145, 147, 148, 606/144, 113; 289/1.2, 1.5, 2, 17; 604/167, 256, 405

[56] References Cited

U.S. PATENT DOCUMENTS

| | | | |
|---|---|---|---|
| 3,871,379 | 3/1975 | Clarke | 606/148 |
| 3,994,287 | 11/1976 | Turp et al. | |
| 4,177,814 | 12/1979 | Knepshield et al. | |
| 4,602,635 | 7/1986 | Mulhollan et al. | |
| 4,610,242 | 9/1986 | Santangelo et al. | |
| 4,610,674 | 9/1986 | Suzuki et al. | |
| 4,641,652 | 2/1987 | Hutterer et al. | 606/148 |
| 4,760,848 | 8/1988 | Hasson | 606/206 |
| 4,923,461 | 5/1990 | Caspari et al. | |
| 4,966,587 | 10/1990 | Baumgart | |
| 5,066,285 | 11/1991 | Hillstead | |
| 5,112,308 | 5/1992 | Olsen et al. | |
| 5,114,408 | 5/1992 | Fleischhaker et al. | |
| 5,144,961 | 9/1992 | Chen et al. | 606/148 |

Primary Examiner—Stephen C. Pellegrino
Assistant Examiner—Gary Jackson
Attorney, Agent, or Firm—Townsend and Townsend Khourie and Crew

[57] ABSTRACT

A suturing device includes a shaft with a pair of axial passages extending through the shaft. A length of suture passes through the first axial passage, the suture having a surgical needle attached to its distal end, and a preformed knotted loop disposed at a distal end of the first axial passage. The second axial passage includes a gaseous seal and is configured to receive a surgical instrument for manipulating tissue to facilitate application of the suture. In the method of the invention, the suturing device is inserted through a cannula and a surgical instrument is introduced through the second axial passage. Tissue is manipulated using the surgical instrument to facilitate application of the suture. A needle holder introduced through a separate cannula is used to pass the needle through the wound and through the knotted loop. Tension is then applied to the suture to close the knot and bind the wound.

31 Claims, 9 Drawing Sheets

DUAL FUNCTION SUTURING DEVICE AND METHOD

CROSS-REFERENCE TO RELATED APPLICATION

This application is a continuation-in-part of U.S. patent application Ser. No. 07/638,887 to Noda et al., filed Jan. 7, 1991, issued Jul. 14, 1992, entitled DEVICE AND METHOD FOR APPLYING SUTURE, the complete disclosure of which is incorporated herein by reference.

BACKGROUND OF THE INVENTION

1. Field of the Invention

The present invention relates generally to the structure and use of surgical instruments, and more particularly, to a device and method for applying and knotting suture in locations having limited access.

Least invasive surgical (LIS) techniques, such as laparoscopic, endoscopic, and arthroscopic surgery, are generally performed through small incisions using specialized instruments to perform desired surgical procedures. Usually, the instruments are introduced through a tube, such as a cannula, while the physician observes manipulation of the instruments through specialized imaging equipment, such as laparoscopes, endoscopes, and arthroscopes. Such LIS techniques offer significant advantages over conventional "open" surgical procedures. In particular, the LIS techniques are usually less traumatic, require a shorter recovery time, and are less costly than the corresponding conventional surgical techniques.

While such LIS procedures have been very successful, improvements in the instruments and techniques which are employed will enhance the efficiency of those procedures which are presently performed and potentially extend the application of LIS techniques to new surgical procedures. In particular, it would be desirable to improve the design of LIS instruments so that they are more readily manipulable, better able to perform specific tasks, less likely to expose the patient to inadvertent injury, and the like.

Of particular interest to the present invention are LIS instruments for applying and tying suture at remote locations. Heretofore, the most common approaches for tying suture have been to manually tie a knot in the free ends of the suture outside of the cannula and to push the knot forward through the cannula using a rod or to tie the knot in situ using instruments. While workable, such techniques are time consuming, limit the type of knot which can be formed, and usually require at least two tying steps to form a tight knot. Thus, it would be desirable to provide improved methods and instruments for applying and tying suture at remote locations.

One improvement which has been proposed is the use of preformed knotted loops in suture. Such knotted loops allow the suture to be tied by passing a free end of the suture through the loop and tightening the loop on the suture after the wound has been closed. Such a technique and an instrument for performing the technique are described in U.S. Pat. No. 4,760,848, described further hereinbelow. The instrument described in the '848 patent, however, is deficient in certain respects. In particular, the instrument must release the knotted loop prior to passing the free end of the suture therethrough. Thus, the loop can be temporarily lost by the physician, making tying of the knot problematic.

The instrument described further lacks any capability for tightening the knotted loop to facilitate tying of the free end of the suture. It would be desirable if the instrument carrying the loop were able to hold the knotted loop during the entire procedure and to tighten the knotted loop without the need to employ a separate instrument.

Of further interest to the present invention are LIS instruments used in conjunction with applying and tying sutures. In particular, it is frequently necessary to use tissue manipulation instruments inserted through one or more cannulas in order to manipulate tissue near the surgical site. Such instruments are used, for example, to position tissue for improved visualization, for retraction of tissue near a wound or incision to facilitate suture application and closure, or to cut or remove tissue. Commonly, both a retraction device and a suturing device are used concurrently when applying and tying sutures.

In known techniques, each instrument to be used in an LIS procedure must be inserted through a cannula or other access port into the surgical site. Typically, each instrument to be used concurrently must have a separate access port. While it is possible to position numerous cannulas near the surgical area to provide a sufficient number of access ports, it is desirable to minimize the number of such cannulas in order to minimize traumatic impact on the patient. It would therefore be particularly advantageous if more than a single instrument, such as a suturing device and a tissue manipulation instrument, could be used simultaneously through a single cannula. Preferably, various types of instruments could be used through the cannula while the suturing device remained in position through the same cannula.

2. Description of the Relevant Art

U.S. Pat. No. 4,760,848, describes a surgical instrument having a pair of jaws at a distal end of a tube. The jaws may be used for carrying a surgical needle which is attached to a length of suture. The suture may have a preformed loop with a slip knot that allows the suture to be tied by passing the needle back through the loop. U.S. Pat. Nos. 4,923,461 and 4,602,635, describe surgical knotting devices where a knot is tied externally and the knot pushed forward to the tissue being sutured. Other remote surgical knotting devices are described in U.S. Pat. Nos. 4,641,652 and 3,871,379.

SUMMARY OF THE INVENTION

According to the present invention, a dual function suturing device comprises a shaft having proximal and distal ends and a first axial passage, suture applying means on the shaft including a length of suture and a surgical needle secured to the distal end of the suture, means at the proximal end of the shaft for selectively applying tension on the proximal end of the suture, and a gaseous seal in the first axial passage, the gaseous seal being operative with and without a surgical instrument received in the axial passage.

Usually, the suturing device further includes a second axial passage through the shaft having a distal port at its distal end. Preferably, the suture has a preformed knotted loop spaced proximally from the needle and slidably disposed in the second axial passage with the surgical needle and knotted loop extending from the distal port in the second axial passage. The knotted loop may be held against the port and closed by applying tension on the proximal end of the suture.

In order to prevent leakage of insufflation fluid from the body cavity, a gaseous seal is provided in the first axial passage. The gaseous seal usually comprises a compliant diaphragm with a slit through it for inserting a surgical instrument. The gaseous seal is thereby operative both with and without an instrument inserted through the passage.

In an exemplary embodiment, grasping forceps are removably disposed in the first axial passage such that the jaws of the forceps extend distally from the distal end of the passage, and the handles of the forceps are disposed proximally of the passage for actuation by the user. The grasping forceps may be used to manipulate tissue near the target site while the suturing device remains in position.

In a preferred embodiment, the means for selectively applying tension comprises an axially aligned track, a handle slidably received in the track, and means on the handle for retaining the proximal end of the suture.

In a further embodiment, the suturing device further includes a sheath slidably disposed on the shaft which can be moved to a distal position to surround the needle and knotted loop in order to facilitate insertion through a cannula without interfering with the needle and suture. The sheath is preferably configured to engage the cannula such that the suturing device may be extended distally of the sheath once the distal end of the device is through the cannula.

According to the method of the invention, the distal end of a shaft is introduced proximate a wound, wherein the distal end carries a length of suture. A surgical instrument is manipulated through a first axial passage in the shaft, with a distal end of the instrument extending from a distal end of the passage. A surgical needle attached to a distal end of the suture is passed through the tissue across the wound, and a loop is formed in the suture through the wound. Finally, a slip knot in the suture is slid distally to close the loop and bind the wound.

Preferably, the surgical instrument comprises grasping forceps, which are used to manipulate tissue near the wound to facilitate applying the suture.

Usually, the suture will have a knotted loop carried at a distal end of the shaft. The slip knot is formed by passing the surgical needle through the knotted loop while the knotted loop remains on the distal end of the shaft, and applying axial tension on a proximal portion of the suture to close the knotted loop against the distal end of the shaft. Preferably, the axial tension is applied using a handle which is slidably attached to the shaft.

Usually, the surgical needle is retained on the shaft while the shaft is introduced, preferably with a slidable sheath surrounding the needle to facilitate introduction without interference with the cannula. The needle is subsequently manipulated, usually with a needle holder. After a suture has been applied, the needle may be removed from the body cavity by pulling it through the first axial passage of the shaft using, for example, the grasping forceps.

DESCRIPTION OF SPECIFIC EMBODIMENTS

The device and method of the present invention are useful for applying and tying suture in a wide variety of surgical procedures, being most useful where the suturing is to be performed in regions with limited accessibility. The present invention will find its greatest use in the performance of laparoscopic, arthroscopic, and endoscopic surgery where the suturing device is introduced and manipulated through relatively narrow cannulas, typically having a diameter of five millimeters or less. Particular procedures which may be performed using the present invention include coapting tissue, where the opposed lips of a wound are joined together after an accidental tear or dissection; ligating vessels or ducts where the suture is passed around a structure and cinched sufficiently tight to occlude the structure so that it can be transected without leakage; anchoring a cannula within a vessel or duct by suturing around the periphery; repairing an access hole left after the removal of a cannula or catheter; retracting of obstructing tissue or organs by cinching the suture loop around said tissue or organ; forming a continuous or running stitch after an initial knot is formed using the knotted loop; repair of bleeding blood vessels; and securing of grafts for hernia repair, anti-adhesion, and the like. Other uses within the spirit of the present invention will occur to those skilled in the art.

The device of the present invention will include a preselected length of suture having a surgical needle attached at one end and a knotted loop formed at a location proximal to the surgical needle. The length of the suture may vary widely, typically being from about 30 to 100 cm, more typically being from about 40 to 60 cm. The preformed knotted loop will typically be spaced-proximally of the surgical needle by a distance in the range from about 4 to 20 cm, usually being in the range from about 10 to 15 cm. The suture may be formed from any conventional surgical suture material, such as silk, wire, gut, and the like. The surgical needle will be a conventional needle, typically having a curved profile to facilitate stitching of a wound using conventional needle holders or forceps.

The loop in the suture will be formed by tying a slip knot in the suture to leave a loop having a target hole therethrough. The diameter of the loop is not critical, typically being in the range from about 5 to 20 mm, more typically being in the range from about 8 to 15 mm.

The knot which forms the loop will be a slipknot, such as a conventional hangman's knot. A particular slipknot which has been found to be suitable for use in the present invention is discussed and illustrated hereinafter. The knot allows the loop to be cinched tight about the free distal end of the suture which is passed back therethrough, forming a particularly secure final knot in the tissue. The loop can be closed by pulling on at least one of the suture ends while the knot is held in place.

The device of the present invention will comprise a shaft having proximal and distal ends. The shaft may have any cross-sectional (peripheral) shape, usually having a round circumference, i.e., being a rod or a cylinder. The diameter of the shaft will usually be of a size to allow passage through a cannula having an opening of ten millimeters or less.

The shaft will have a first axial passage for receiving a surgical instrument. The first axial passage will have a gaseous seal, usually at the proximal end, for preventing leakage of insufflation fluid from the body cavity. The gaseous seal will be operable to prevent such leakage both when an instrument is received in the passage, and when no instrument is received therein. The size of the first axial passage will usually be at least five millimeters in diameter to accommodate surgical instruments of such size.

A surgical instrument may be removably received in the first axial passage. The surgical instrument may be any of a variety of instruments, such as retraction devices, incising tools, or other manipulation instruments. Preferably, the surgical instrument will be grasping forceps used to manipulate tissue around a wound to facilitate application of the suture. The grasping forceps usually will have a pair of jaws extending distally of the first axial passage, and a pair of handles extending proximally of the passage for actuation by the user.

The shaft will include means for holding the length of suture in axial alignment therewith. Typically, the holding means will comprise a second axial passageway extending from the proximal to the distal end of the shaft, but could also consist of an external structure on the shaft for holding the suture in the desired alignment.

The shaft will further have means for securing and applying an axial tension to a proximal end of the suture which is being held on the shaft. Usually, the tensioning means will comprise a slidable handle which allows the user to manually apply the desired axial tension. Other mechanisms, such as levers, scissors, pull-rings, and the like, could be used to either manually or automatically apply the desired tension, but such structures are generally less desirable than the use of the slidable handle.

The knotted loop and needle on the length of suture will extend from the distal end of the shaft, and a means will be provide at the distal end of the shaft for holding the loop against the distal tip of the shaft as axial tension is applied, e.g., using the slidable handle just described. Typically, the means for holding the knotted loop will comprise a port or orifice formed in the distal tip of the shaft, where the diameter of the opening is selected to permit free passage of the suture, but block passage of the knot in the suture, i.e., the port or orifice will have a diameter larger than the suture but smaller than the knot. Thus, because of the nature of the slipknot, pulling on the proximal end of the suture will close the loop while the knot is held stationary against the distal tip of the shaft.

Conveniently, the shaft will include means at or near its distal end for carrying the needle to facilitate introduction and removal of the device through a cannula or other limited access port. The shaft will usually also include means for detachably securing the free end of the preformed loop as well as the region of the suture between the loop and the surgical needle which would otherwise be loose and subject to entanglement. The means for securing the needle will also be useful for tensioning the distal end of the suture as the suture is trimmed after tying. Specific structures for providing such securing means are described in detail hereinafter in reference to the figures.

The suture applier will further include means for enclosing the needle and knotted loop at the distal end of the shaft to facilitate insertion through a cannula without interference. The means for enclosing the needle and knotted loop will usually comprise a sheath slidably disposed on the shaft. The sheath may be moved to a distal position where it surrounds the needle and knotted loop for insertion through the cannula. Usually, the sheath will have a rim on its proximal end to engage the cannula such that the distal end of the shaft may be extended distally beyond the sheath once it has passed through the cannula. The material used for the sheath is not critical so long as it has sufficient rigidity to provide protection for the needle and maintains its form when inserted through a cannula. Typically, the sheath will be a surgical metal such as stainless steel, or a biocompatible plastic.

The suture applier of the present invention will usually be a single-use device which, after fabrication, is sterilized and placed in sterile packaging. Alternatively, it would be possible to reuse the shaft portion of the device (after sterilization) by replacing the length of suture having the preformed knot and surgical needle. Thus, the present invention includes the suture needle. Thus, the present invention includes the suture itself having the particular slip knot which is described hereinafter, usually present in sterile packaging.

Referring now to FIGS. 1-4, a suture applying device 10 constructed in accordance with the principles of the present invention will be described. The suture applier 10 includes a shaft 12 having a proximal end 14 and a distal end 16. A length of suture 18 extends from the shaft 12 through a port 20 (FIG. 3) at the distal end of shaft. Surgical needle 22 is attached to a distal end of suture 18 and is removably secured through a slot 24 and into a first elastic band 26 and silicone rubber insert tube 28. It will be appreciated that the surgical needle 22 can be pulled out through port 24 by pulling on the protruding end, as will be described in more detail hereinafter.

Figures 1, 2, 3:
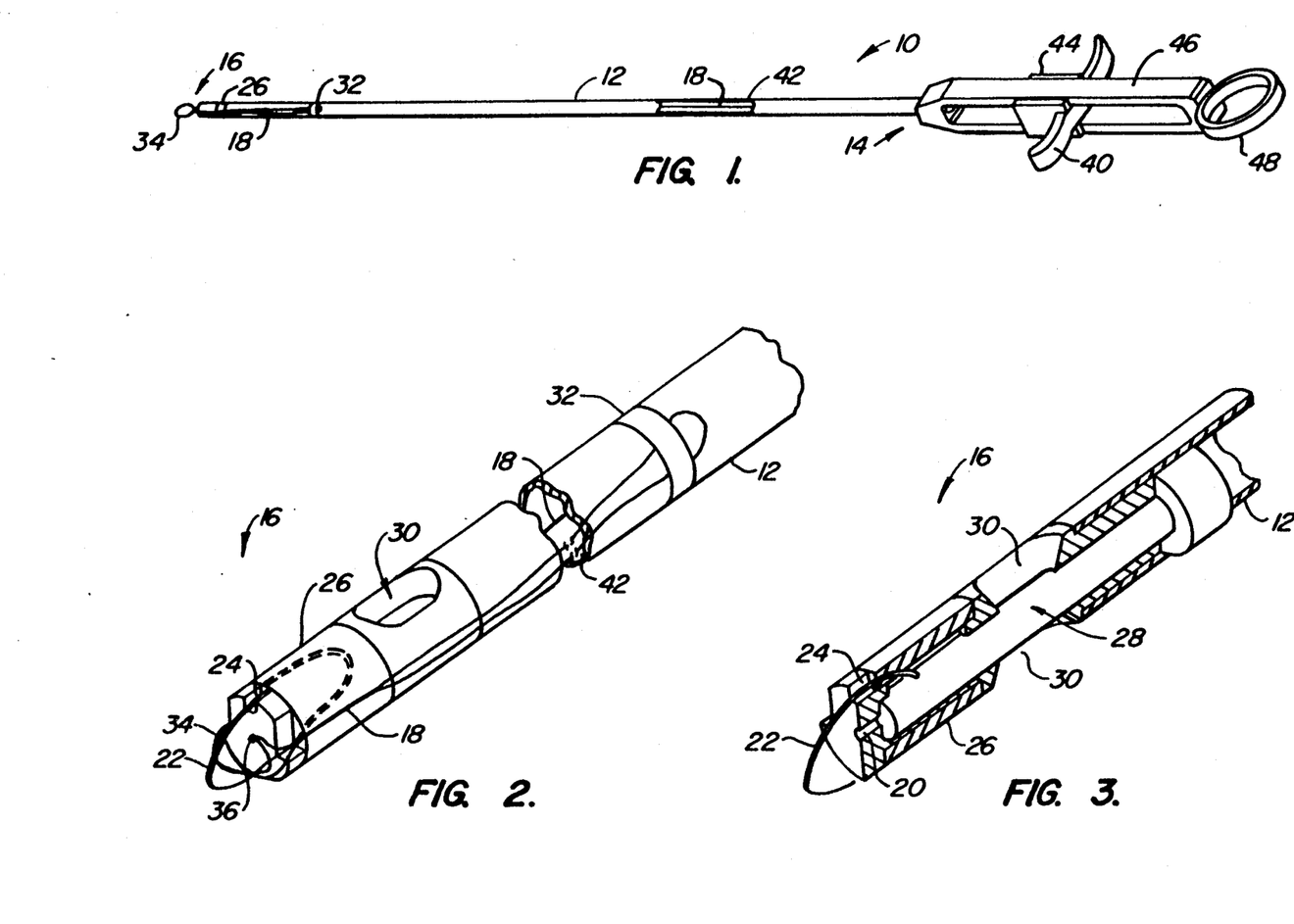
FIG. 1 is a perspective view of a suture applier constructed in accordance with the principles of the present invention.
FIG. 2 is a detailed view of the distal end of the suture applier of FIG. 1.
FIG. 3 is a cross-sectional view of the distal end of the suture applier of FIG. 1.

A pair of opposed access ports 30 are formed on opposite sides of the shaft 12 a short distance proximal from the distal end 16. The ports 30 are intended to provide a means for securing the needle as the device is withdrawn from use, as will be described in more detail hereinafter. The needle 22 is simply passed through one of the two ports 30 and penetrated into the silicone rubber tube 28 where it will be retained until it is removed.

A second elastic band 32 is formed a short distance proximally from the distal tip of the shaft 12. The distance is usually in the range from about 2 to 10 cm, more usually being in the range from about 5 to 8 cm. The elastic band 32 is intended to allow the length of suture 18 between a knotted loop 34 and the surgical needle 22 to be detachably secured to the shaft 12.

As best observed in FIG. 2, the knotted loop 34 includes a slipknot 36 (as will be described in more detail hereinafter) which is generally held at the distal port 20. The loop 34 will thus extend from the distal end of the shaft 12, as best observed in FIG. 1. The loop 34, however, may be detachably secured (folded back) beneath the elastic band 26, as illustrated in broken line in FIG. 2.

Figure 4:
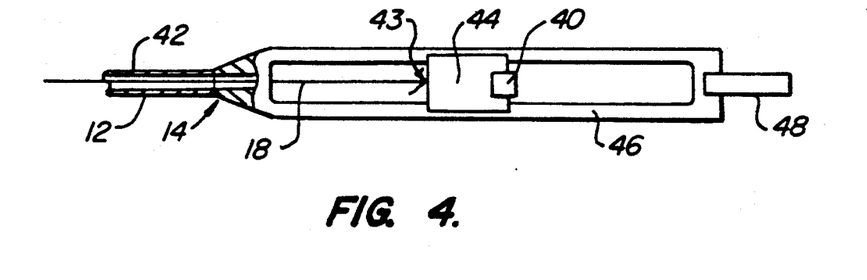
FIG. 4 is a side-elevational view of the proximal end of the suture applier of FIG. 1.

A slidable handle 40 is located at the proximal end 14 of the shaft 12 in order to provide an axial tension on the suture 18. Suture 18 extends in a proximal direction from port 20 through an axial passage 42 in tube 12 and is secured at its proximal end 43 to a sliding block 44 which is attached to the handle 40. Sliding block 44 is capable of axially translating within a track defined by an open frame 46 which is attached to the proximal end of the tube 12. A thumb ring 48 is conveniently provided at the proximal end of the frame 46. In this way, the user can hold the suture applier 10 in one hand with the user's thumb in thumb ring 48 and the index finger and forefinger engaged in opposition to the thumb against the handle 40. Tension may be applied on suture 18 then by simply pulling on the handle 40 with the fingers against to the thumb. This structure allows very precise control on the tension and facilitates closing loop 34 to form a tight knot, as described in more detail hereinafter.

Figure 4A:
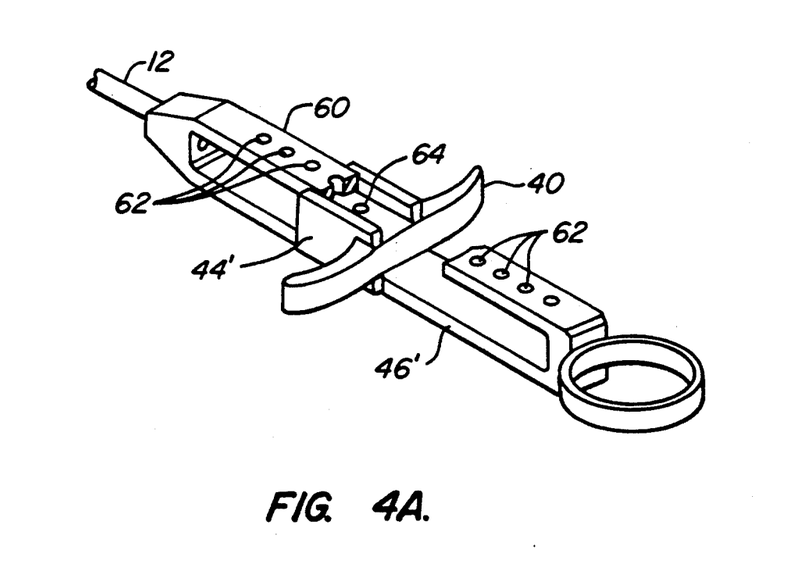
FIG. 4A is a detailed perspective view of the proximal end of an alternate embodiment of a suture applier constructed in accordance with the principles of the present invention.

An alternate embodiment of the proximal end of the suture applier is illustrated in FIG. 4A. The proximal end includes a slidable handle 40' attached to sliding block 44' which is slidably received in a track defined by open frame 46'. The track 46' includes a top rail 60 having a plurality of spaced-apart detent holes 62 formed therein. A spring-loaded ball 64 is located on sliding block 44' and aligned so that it can selectively engage the detent holes 62 as the handle 40 is translated forward and backward in the track 46'. The detents allow the handle to be "ratcheted" in the proximal direction so that the treating physician can incrementally apply tension to the suture. The detents will hold the handle at a desired level of tension, reducing muscle fatigue in the physician's hand.

Figure 5A:
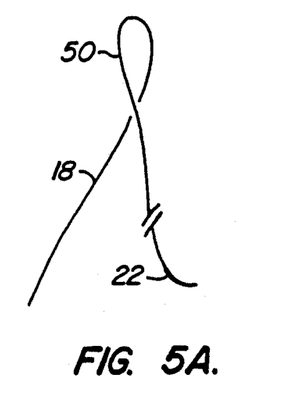
FIGS. 5A-5E illustrate the steps for tying the preferred slipknot for forming the knotted loop in the suture of the present invention.
Figure 5B:
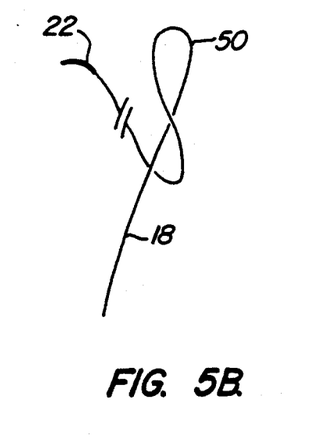
Figure 5C:
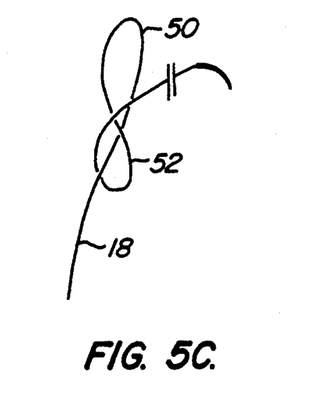
Figure 5D:
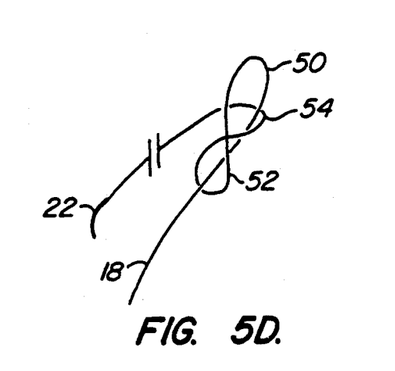
Figure 5E:
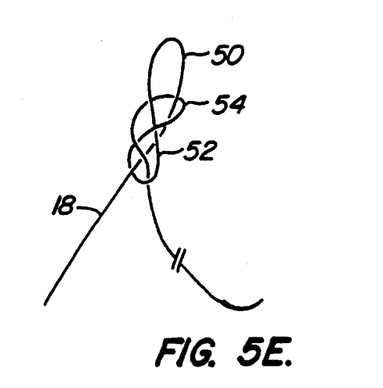

Referring now to FIGS. 5A-5E, the steps for forming the preferred slipknot 36 of the present invention will be described. The distal end of suture 18 having the attached surgical needle 22 is doubled over to form a first loop 50, as illustrated in FIG. 5A. The needle 22 is then pulled back around the proximal portion of suture 18 (FIG. 5B) and then brought around to cross over the front of the suture 18 to form a second loop 52 (in a figure eight pattern with first loop 50), with the proximal length of suture 18 passing through the second loop 52. The needle 22 is next brought around the back of the emerging knot structure to form a third loop 54 (FIG. 5D) which encircles the crossover region between loops 50 and 52. The needle is then brought through the lower loop 52 in order to complete the slipknot structure.

Figure 6:
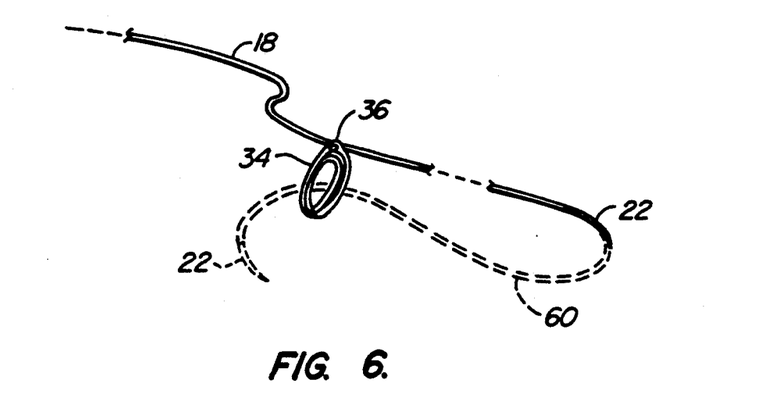
FIG. 6 illustrates a length of suture having the preferred slipknot and loop formed therein with a surgical needle at its distal end.

Suture 18 having loop structure 34 and slipknot 36 therein is illustrated in FIG. 6. It will be appreciated that the loop structure 34 corresponds to the loop 50 formed as ILLUSTRATED IN figs. 5A-5E which has been doubled over to form a double loop. The slipknot 36 is formed from loops 52 and 54, and the proximal end (i.e., to the left in FIG. 6) of the suture 18 can be pulled through the slip knot to tighten and close the loop 34.

To form the final suture knot according to the present invention, the needle 22 is passed through the interior of loop 34, as illustrated in broken line in FIG. 6. The loop 34 is then tightened by pulling on the proximal end of suture 18 as just described. A secondary loop 60 which is formed when the needle 22 is passed through the first loop 34 may then be tightened by pulling on the distal or needle end of the suture 18. As described in more detail hereinafter, it is this secondary loop which actually forms the suture stitch in the wound being closed.

Figure 7A:
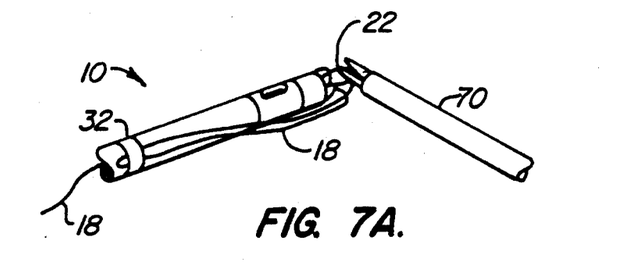
FIGS. 7A-7G illustrate the method of the present invention using the suture applier of FIG. 1 to suture and tie a wound in tissue.
Figure 7B:
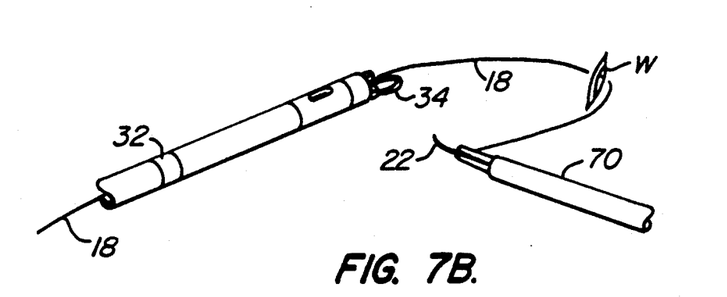

Referring now to FIGS. 7A-7G, the method of the present invention will be described Initially, the suture applier 10 is removed from its sterile packaging to the sterile field using standard aseptic techniques. The suture applier 10 is then introduced through a cannula or other access tube to a region of interest, typically near a wound to be sutured. A needle holder 70 is introduced to the same region through a second cannula or other access tube and the needle 22 is grasped and removed from its port on the suture applier 10 (FIG. 7A).

After removing the needle 22, the excess length of suture 18 between the loop 34 and the needle is removed from elastic band 32, and the needle is then passed through the tissue on either side of a wound W (FIG. 7B) in a conventional manner. The needle 22 is then brought through the loop 34 (FIG. 7C) to form a secondary loop 72.

Figure 7C:
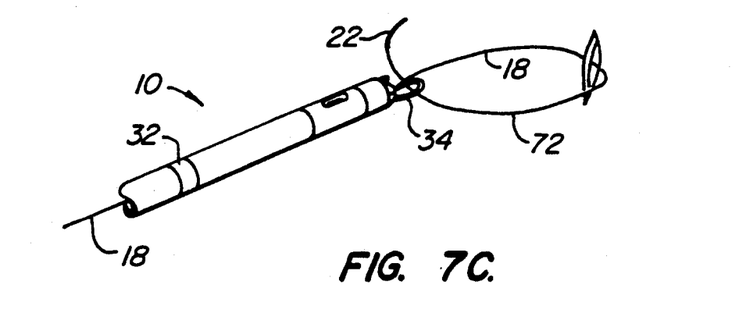
Figure 7D:
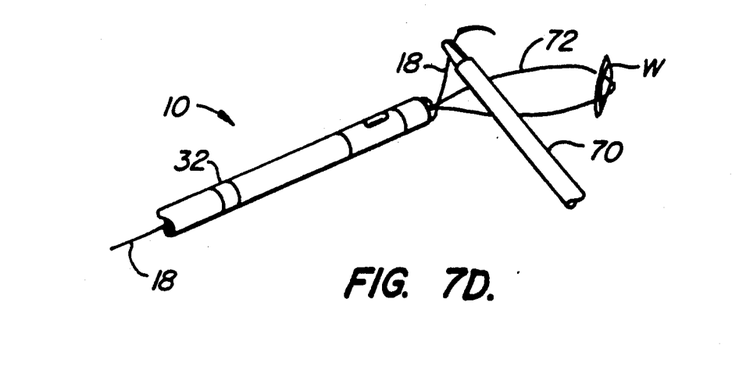
Figures 7E, 7F:
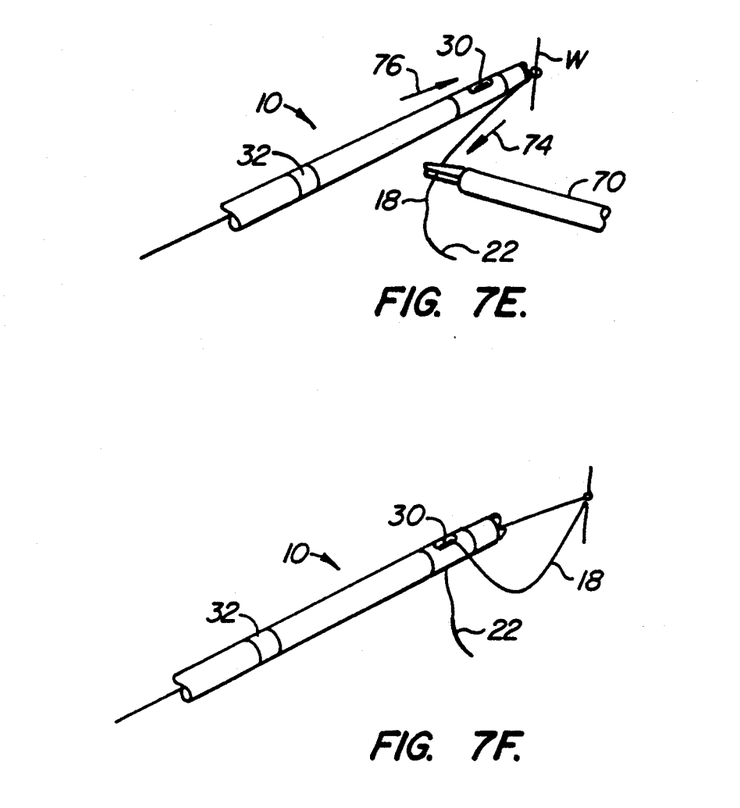

After forming the secondary loop 72, the distal end of suture 18 is held in place with the needle holder 70, and the handle 40 is used to apply tension on the proximal end of suture 18 in order to close loop 34 about the suture 18 passing therethrough (FIG. 7D). The secondary loop 72 is then closed by pulling on the distal end of suture 18 in the direction shown by arrow 74 (FIG. 7E), while the suture applier 10 is used to apply a counter force in the direction of arrow 76. After the secondary loop 72 has been tightened to close the wound W, the (primary) loop 34 may be further tightened by applying additional tension on the handle 40. After the loop 34 is tightened to a sufficient degree, tension on the suture 18 may be released (FIG. 7F), and the needle 22 will be passed through the needle ports 30. The tail ends of suture 18 extending from the tied suture knot will then be clipped (conveniently using the applier 10 to pull back on the tail ends so that they can be cut using conventional scissors), and the suture applier 10 may be removed through the cannula with the needle being carried out with the suture applier.

Figure 7G:
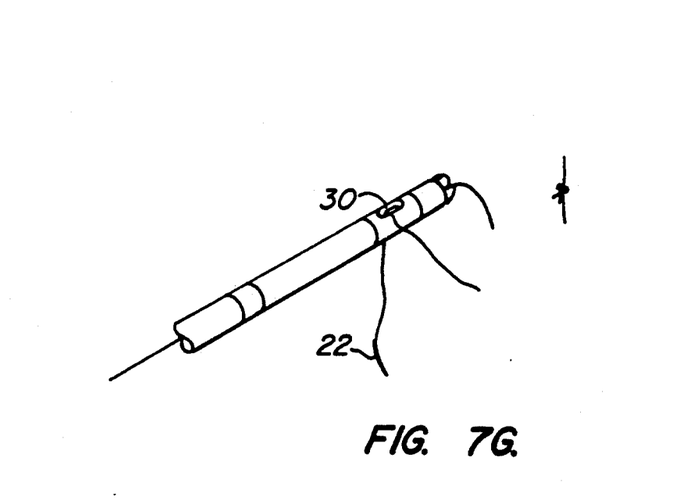
Figure 8:
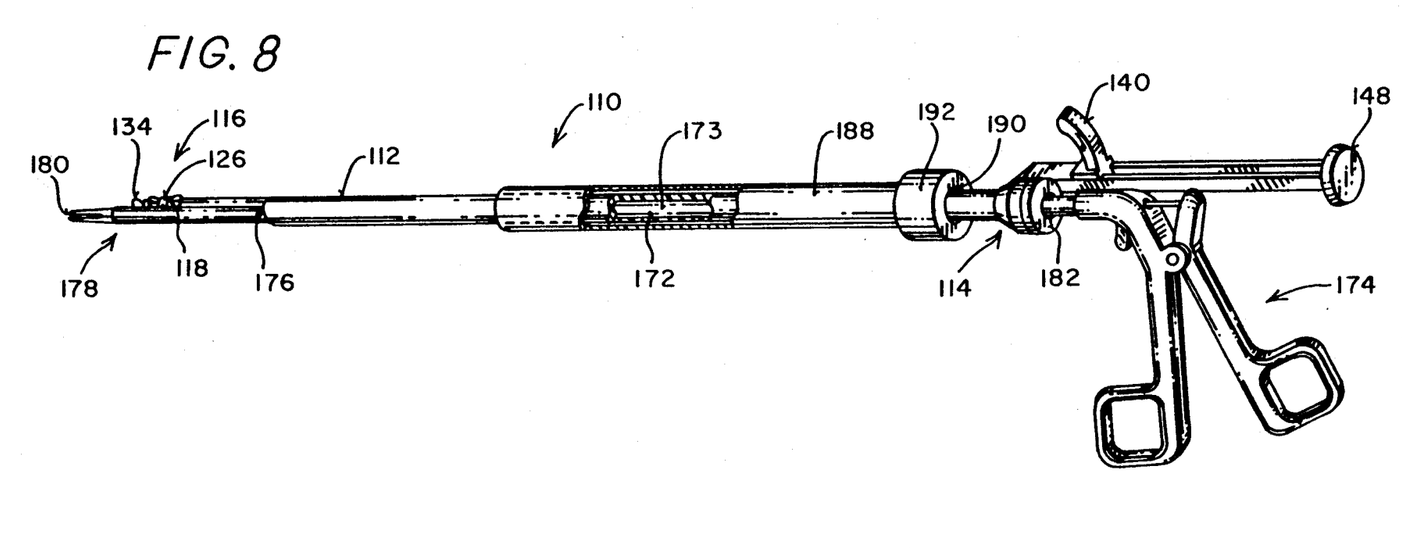
FIG. 8 is a perspective view of a suturing device constructed in accordance with the principles of the present invention having a surgical instrument received therein.

A continuous suture may be formed by securing a knot as described above with reference to FIGS. 7A through 7E, but proceeding with additional stitches prior to trimming the suture, as illustrated in FIG. 7G. The continuous stitch is terminated by performing an instrument tie after the final stitch is thrown, in a conventional manner. Retrieval of the instrument is performed in the same manner as described with reference to FIG. 7G.

A further embodiment of the suturing device of the present invention will now be described with reference to FIGS. 8-13. In this embodiment, suturing device 110 has pair Of parallel axial passages 142, 172 through a shaft 112 (shown more clearly in FIG. 10). One of the axial passages will be dedicated to suture application, while a second will be a multi-function passage for receiving various types of surgical instruments, as described below.

Figure 9A:
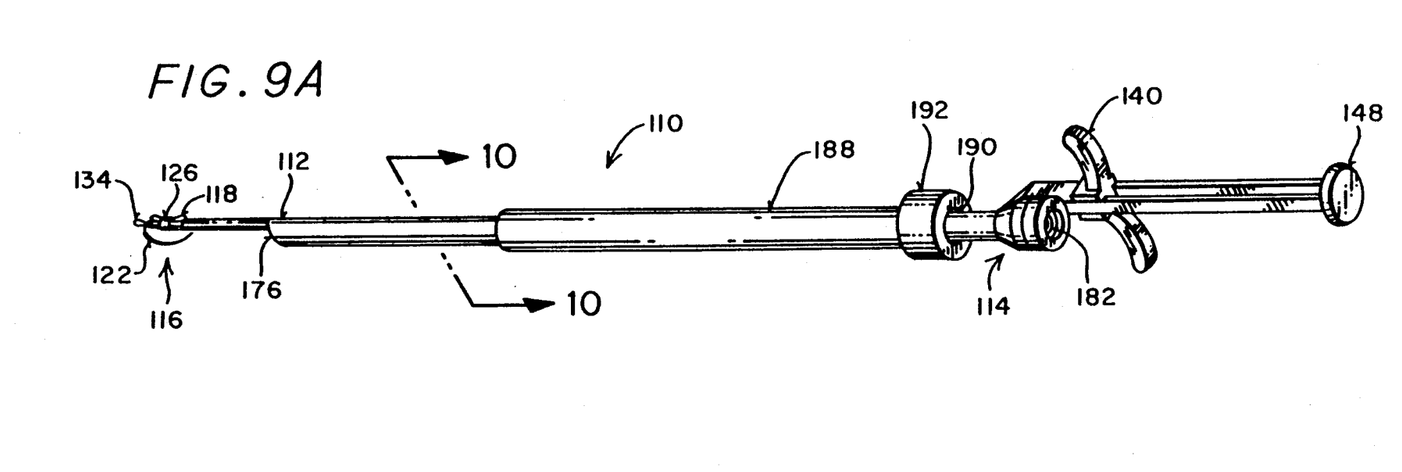
FIG. 9A is a perspective view of the suturing device of FIG. 8 without a surgical instrument received therein.

A length of suture 118 is disposed in a first axial passage 142 in generally the same manner as described above with reference to FIGS. 1-4. Referring to FIGS. 9A-/B, suture 118 has a preformed knotted loop 134 disposed distally of a distal port 120 in axial passage 142, with port 120 being of a size to prevent the knot from passing therethrough. Knotted loop 134 will be formed in a manner like that described above with reference to FIGS. 5A-5E. One or more loops in suture 118 are retained under an elastic cuff 126 disposed near a distal end 116 of shaft 112, cuff 126 being of a biocompatible elastomer such as silicone rubber. A surgical needle 122 is attached to the distal end of suture 118. Distal end 116 of the shaft may further include means for retaining needle 122 (not shown) while the suturing device is being introduced near the surgical site. The means for retaining the needle may comprise, as shown in FIG. 2, a slot in the distal end of the shaft and an insert tube of penetrable material, such as silicone rubber, within the shaft behind the slot into which the needle may be penetrated.

Figure 11:
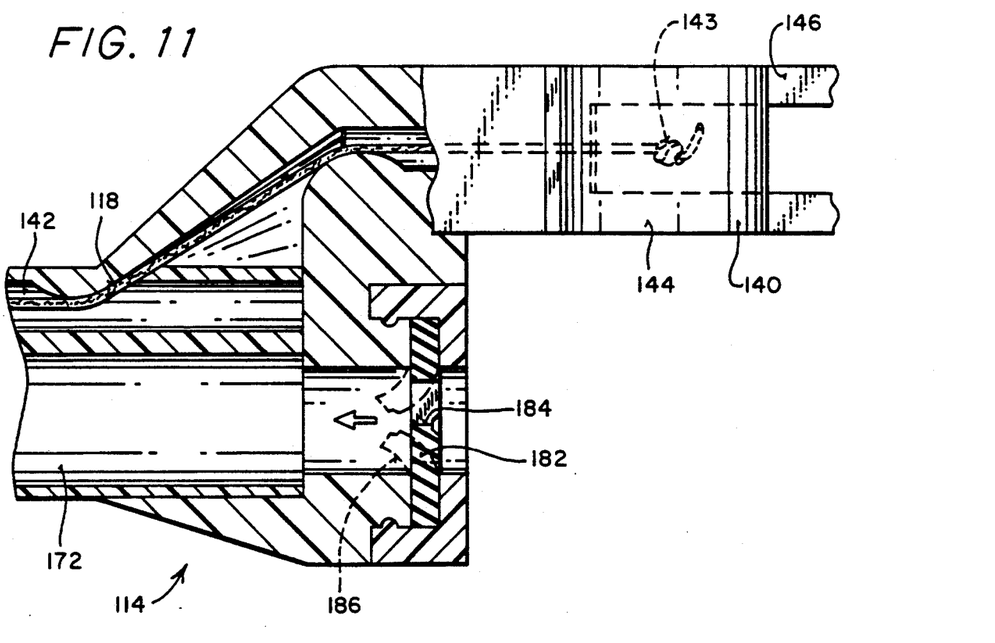
FIG. 11 is a side cross-section of the proximal end of the suturing device of FIG. 9A.

Referring to FIG. 11, a proximal end 143 of suture 118 is attached to a slidable handle 140 at the proximal end of the shaft for selectively applying tension to suture 118. Slidable handle 140 will generally be constructed as described above with reference to FIGS. 4-4A, except that the handle will be disposed in a position slightly offset from the center of shaft 112 in order to allow a surgical instrument to be inserted into axial passage 172 adjacent handle 140. The handle will include a sliding block 144 to which proximal end 143 of suture 118 is connected, the sliding block being capable of axial translation relative to an open frame 146. A thumb rest 148 is disposed at the proximal end of frame 146, which is shown in the figure as a button, but which may also be configured as a ring or other structure to which thumb pressure may be applied. In this way, the user may apply axial tension to suture 118 by applying axial force using two fingers on handle 140 in opposition to pressure by the thumb against thumb rest 148. It will be understood that a variety of alternative structures may be used to apply tension to suture 118, including, for example, pull-rings, pivotable handles, and other such mechanisms.

Referring again to FIGS. 8-10, a second axial passage 172 extends through shaft 112 parallel to axial passage 142, through which a surgical instrument 174 may be inserted. For purposes of illustration, surgical instrument 174 is shown as grasping forceps, which have particular usefulness in facilitating application of sutures, as described more fully below. However, it will be understood that surgical instrument 174 may comprise any of a variety of surgical instruments, for example, manipulation and retraction instruments, cutting tools and the like.

Second axial passage 172 terminates at a distal port 176 (FIG. 9B), from which a distal end 178 of grasping forceps 174 extends. Axial passage 172 will have a diameter suitable for receiving conventional surgical instruments for use in LIS procedures, typically five millimeters. Grasping forceps may be of any known design having an elongated configuration appropriate for insertion through axial passage 172. Grasping forceps 174 have a pair of movable jaws 180 coupled to a distal end of an elongated member 173, jaws 180 being disposed distally of the distal end 116 of the shaft to allow access to a desired tissue site. Jaws 180 are actuated by a pair of handles at the proximal end of grasping forceps 174, wherein movement of the handles relative to one another closes or opens jaws 180.

Figure 10:
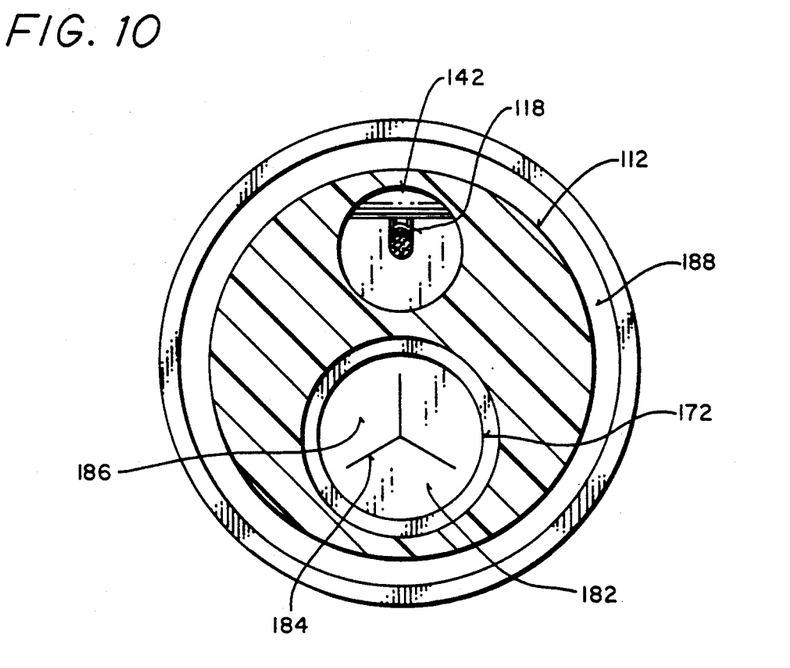
FIG. 10 is a transverse cross-section of the shaft of the suturing device of FIG. 9A.

Of particular importance in LIS procedures is the retention of insufflation fluid within the body cavity. Normally, the cannula through which suturing device 110 is introduced will have sealing means for preventing fluid leakage about the periphery of the suturing device. To prevent leakage through the second axial passage 172, a gaseous seal 182 is provided in axial passage 172 at the proximal end 114 of shaft 112. As shown in FIGS. 10-11, the gaseous seal comprises a disk of a compliant material, such a silicone rubber, with a slit 184 through a central portion of the disk to permit insertion of surgical instrument 174. Slit 184 may comprise a tri-cuspid form as shown in FIG. 10, as well as bi-cuspid or other configuration. Slit 184 defines a plurality of flexible flaps 186 which contact each other to create a seal when no instrument is received in axial passage 172. With instrument 174 inserted through gaseous seal 182, flaps 186 are pushed distally and radially, the compliant flaps conforming to the peripheral shape of elongated member 173 of instrument 174. In this manner, the seal prevents fluid leakage through axial passage 172 both when instrument 174 is received in the passage, as well as when no instrument is received in the passage.

Figures 9B, 12C, 13:
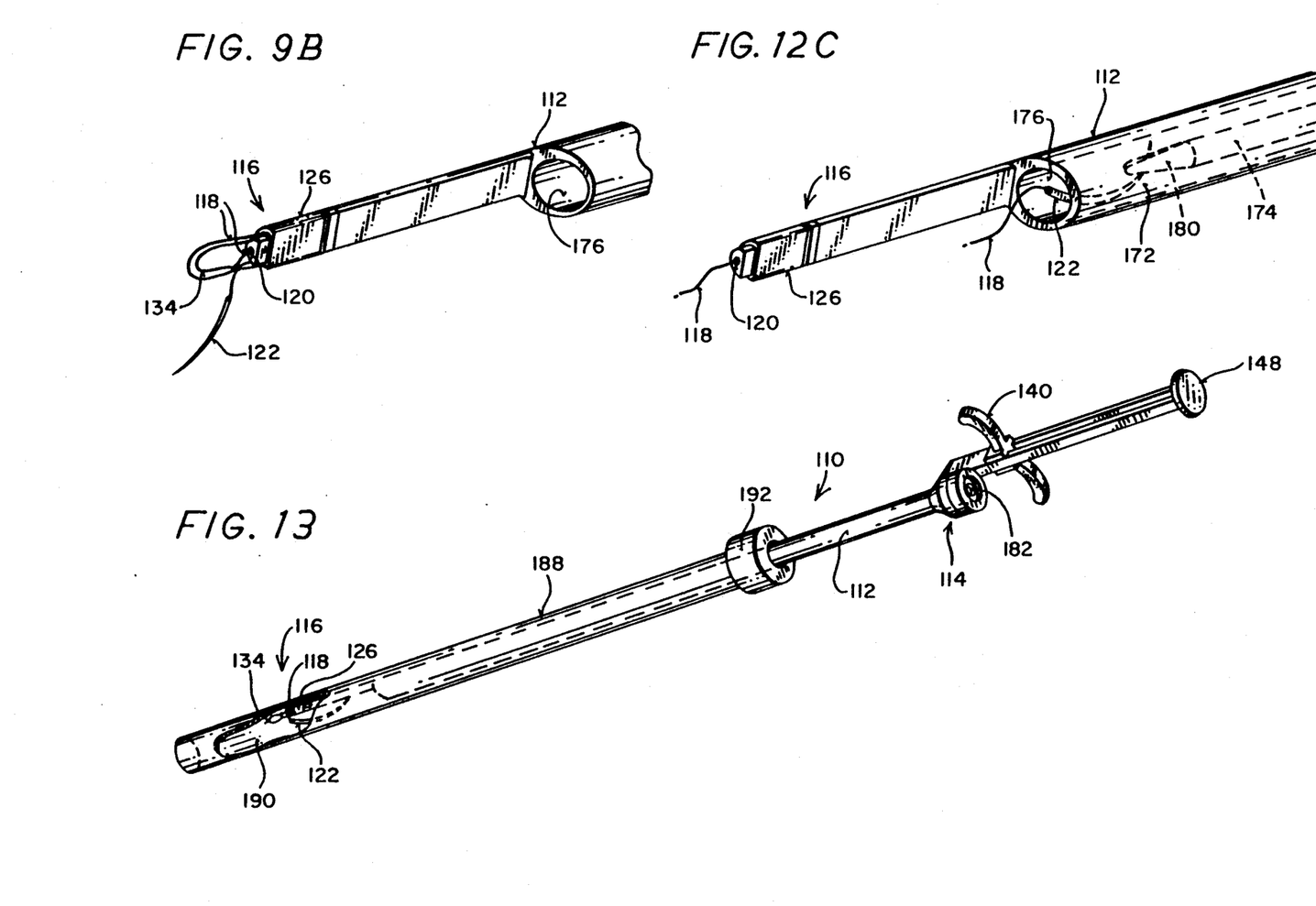
FIG. 9B is a perspective view of a distal end of the suturing device of FIG. 9A.
FIGS. 12B-12C are perspective views of the suturing device positioned as in FIG. 12A illustrating the method of using the suturing device according to the principles of the present invention.
FIG. 13 is a perspective view of the suturing device of FIG. 9A with a sheath positioned to surround the needle and suture to facilitate introducing the suturing device through a cannula.

Suturing device 110 further includes a slidable sleeve 188 disposed about the periphery of shaft 112. The material of sleeve 188 will be surgical metal such as stainless steel or a rigid plastic. As illustrated in FIG. 13, sleeve 188 has a central passage 190 shaped to conform to the periphery of the shaft. Sleeve 188 may be translated distally and proximally along shaft 112. When moved to a distal position, shown in FIG. 13, the sleeve surrounds the distal end 116 of the shaft, including knotted loop 134, needle 122, as well as distal end 178 of surgical instrument 174, to facilitate insertion through a cannula without interference. Sleeve 188 further has a rim 192 at its proximal end which engages a proximal end of the cannula. When rim 192 engages the cannula, sleeve 188 is retained in position in the cannula and the distal end of the suturing device may be extended distally of sleeve 188, thereby exposing knotted loop 134, needle 122 and jaws 189 of grasping forceps 174. The outer diameter of the sleeve will be preferably selected to be insertable through a cannula having an inner diameter of ten millimeters or less. The outer diameter of rim 192 will be larger than the inner diameter of the cannula, in order to engage the proximal end of the cannula.

Figure 12A:
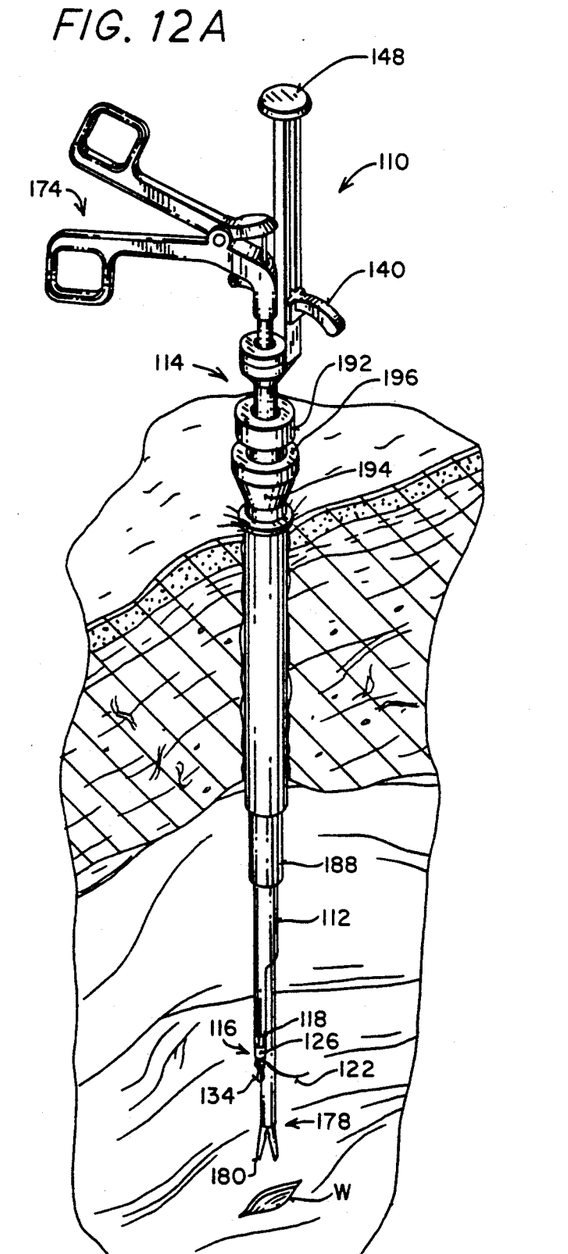
FIG. 12A is a perspective view of the suturing device of FIG. 8 positioned through a cannula into a body cavity.

A further embodiment of the method of the present invention will be described with reference to FIG. 12A-C and 13. The method will preferably be performed as part of a LIS procedure, wherein a body cavity, such as the peritoneum, is insufflated with a gas such as $CO_2$. One or more cannulas 194 will be inserted through the wall of the cavity, as shown in FIG. 12A, providing a sealed accessway into the body cavity. Typically, visualization of the body cavity is provided by a camera introduced through a cannula, the camera connected to a video monitor viewed by the surgeon.

In the method of the invention, suturing device 110 will be removed from its sterile packaging and sleeve 188 translated to the distal position shown in FIG. 13. Needle 122 may be retained in a retaining means such as a penetrable insert in the distal end of shaft 112, if one is provided, as described above. Alternatively, needle 122 may be retained within sleeve 188 between a distal portion of shaft 112 and the inner wall of sleeve 188. At this point, surgical instrument 174 need not be inserted in second axial passage 172 in shaft 112, but may be if desired.

Figure 12B:
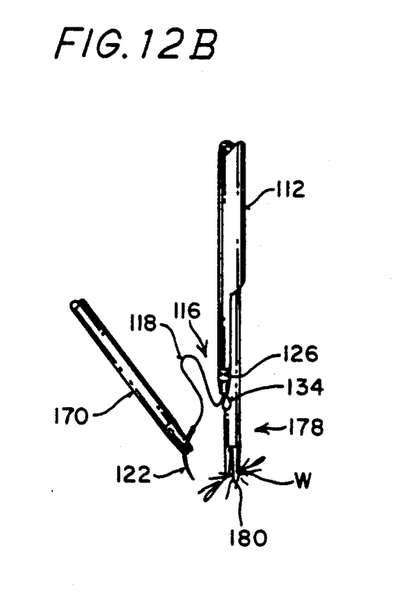

Referring to FIGS. 12A-C, suturing device 110 will be introduced through a cannula 194 so that the distal end of the device is positioned near the surgical site or wound W. Cannula 194 will be of a standard design commonly used in LIS procedures, such as a trocar sleeve. Suturing device 110 is inserted distally such that rim 192 at the proximal end of sleeve 188 engages the proximal end 196 of cannula 194. This inhibits further distal movement of sleeve 188, permitting the distal end of suturing device 110 to be extended distally of sleeve 188 into the position shown in FIG. 12A. A surgical instrument, such as grasping forceps 174, is inserted through seal 182 at the proximal end of shaft 112 and through second axial passage 172, so that the distal end 178 of the instrument extends distally of the distal end 116 of the shaft. As shown in FIG. 12B, a needle holder 70 is then introduced through a separate cannula. The needle holder 70 is used to grasp needle 122 and remove it from the retention means (if provided-see FIG. 7A). The excess length or loops in suture 118 are removed from beneath elastic cuff 126. Grasping forceps 174 are then used to manipulate the tissue near wound W, usually in a manner so as to pull the opposing portions of tissue together so as to facilitate application of the suture.

The application of the suture to wound W will be performed generally as described above with reference to FIGS. 7A-E. Needle holder 170 is used to manipulate needle 122 so as to pass it across wound W so as to form a loop in the suture through the wound, in the manner shown in FIG. 7B. Needle 122 is then passed through knotted loop 134, as shown in FIG. 7C. Axial tension is then applied to the proximal end of suture 118 by actuating handle 140 to close knotted loop 134 about suture 118, as illustrated in FIG. 7D. The wound is bound by pulling on needle 122 to exert tension from the distal end of suture 118, as in FIG. 7E, pushing the slip knot formed in suture 118 distally to close the loop through the wound. Further tightening may be achieved by additional actuation of handle 140.

After the wound has been bound, a cutting device, such as scissors, will be introduced through a separate cannula for cutting suture 118. As illustrated in FIG. 12C, needle 122 and any suture attached thereto may be withdrawn from the body cavity by grasping needle 122 with jaws 180 of grasping forceps 174 and withdrawing needle 122 through axial passage 172. The suture applier may then be removed through cannula 194. Alternatively, the suture applier may remain in position in cannula 194 so that additional procedures may be performed using instruments inserted through axial passage 172.

Although the foregoing invention has been described in detail for purposes of clarity of understanding, it will be obvious that certain modifications may be practiced without departing from the scope of the appended claims.

What is claimed is:

1. A dual function suture applier comprising:
   a shaft having proximal and distal ends and an axial passage;
   suture applying means on the shaft, the suture applying means including a length of suture having proximal and distal ends, and a surgical needle secured to the distal end of the suture;
   means at the proximal end of the shaft for selectively applying tension on the proximal end of the suture; and
   a gaseous seal in the axial passage, the gaseous seal being operative with and without a surgical instrument received in the axial passage.

2. The suture applier of claim 1 wherein the shaft has a diameter of at most 10 mm.

3. The suture applier of claim 2 wherein the axial passage has a diameter of at least 5 mm.

4. The suture applier of claim 1 wherein the gaseous seal means comprises a compliant diaphragm at the proximal end of the axial passage, the diaphragm having a slit through a central portion thereof to facilitate insertion of the surgical instrument.

5. The suture applier of claim 1 further comprising grasping forceps removably disposed in the axial passage, the grasping forceps having a pair of movable jaws extending distally of the axial passage and an actuator coupled to the jaws and disposed proximally of the axial passage.

6. The suture applier of claim 1 wherein the suture applying means further comprises a second axial passage in the shaft having a distal port at a distal end thereof, said suture having a knotted loop spaced proximally from the needle and being slidably disposed in the second axial passage with the surgical needle and knotted loop extending from the distal port in the second axial passage, whereby the knotted loop may be held against the port and closed by applying tension on the proximal end of the suture.

7. A dual function suture applier comprising:
   a shaft having proximal and distal ends, a first axial passage having a first distal port and a second axial passage having a second distal port;
   a length of suture having proximal and distal ends, a surgical needle secured to the distal end of the suture, and a knotted loop disposed proximally of the needle, said suture being slidably disposed in the second axial passage with the surgical needle and knotted loop extending from the second distal port at the distal end of the second axial passage;
   means at the proximal end of the shaft for securing and selectively applying tension on the proximal end of the suture, whereby the knotted loop may be held against the port and closed by applying such tension; and
   a gaseous seal in the first passage, the gaseous seal being operative with and without a surgical instrument received in the first passage.

8. The suture applier of claim 7 wherein the shaft has a diameter of at most 10 mm.

9. The suture applier of claim 8 wherein the first axial passage has a diameter of at least 5 mm.

10. The suture applier of claim 7 wherein the gaseous seal means comprises a compliant diaphragm at the proximal end of the first axial passage, the diaphragm having a slit through a central portion thereof to facilitate insertion of the surgical instrument.

11. The suture applier of claim 7 further comprising grasping forceps removably disposed in the first axial passage, the grasping forceps having a pair of movable jaws extending distally of the first distal port and an actuator coupled to the jaws and disposed proximally of the first axial passage.

12. The suture applier of claim 7 further comprising a sheath slidably disposed on the shaft, whereby the sheath may be moved to a distal position to surround the needle and the knotted loop to facilitate insertion of the suture applier through a cannula.

13. The suture applier of claim 12 wherein the sheath has a rim on a proximal end thereof for engaging a proximal end of the cannula, whereby the sheath may be advanced together with the suture applier through the cannula until the rim engages the cannula, allowing the suture applier to be advanced distally relative to the sheath to extend the needle and knotted loop beyond a distal end of the sheath.

14. A suture applier as in claim 7 wherein the means for selectively applying axial tension includes an axially aligned track, a handle slidably received in the track, and means on the handle for retaining the proximal end of the suture.

15. A suture applier as in claim 7 further comprising means at the distal end of the shaft for removably securing the surgical needle.

16. A suture applier as in claim 15, wherein the means for removably securing the surgical needle comprises a port in the distal tip of the shaft having penetrable material behind the port.

17. A suture applier as in claim 16, further comprising an additional port in a side wall of the shaft having penetrable material behind said port, whereby the surgical needle can be secured after use and the suture can be tensioned to facilitate trimming of the tail ends after the suture is tied.

18. A suture applier as in claim 7, further comprising means at the distal end of the shaft for detachably securing a free end of the knotted loop.

19. A suture applier as in claim 18, wherein the means for detachably securing a free end of the knotted loop comprises an elastic cuff disposed about the shaft.

20. A method for suturing a wound in tissue, the method comprising:
introducing the distal end of a shaft proximate said wound, wherein said distal end carries a length of suture;
manipulating a surgical instrument through a first axial passage in the shaft, a distal end of the instrument extending from a distal end of the passage;
passing a surgical needle attached to a distal end of the suture through the tissue across the wound;
forming a loop in the suture through wound; and
sliding a slip knot in the suture distally to close the loop and bind the wound.

21. A method as in claim 20 wherein the surgical instrument comprises grasping forceps.

22. A method as in claim 20 wherein the surgical instrument is used to manipulate the tissue near the wound to facilitate applying the suture.

23. A method as in claim 20 wherein the tissue is in a body cavity insufflated with a fluid, the first axial passage having sealing means to prevent leakage of the fluid when the manipulation instrument is introduced therethrough.

24. A method as in claim 23 wherein the shaft is inserted through a sealed cannula having a diameter of at most 10 mm.

25. A method as in claim 24 wherein the first axial passage has a diameter of less than 8 mm.

26. A method as in claim 20 wherein the suture has a preformed knotted loop carried at the distal end of the shaft, the slip knot being formed by passing the surgical needle through the knotted loop while the knotted loop remains on the distal end of the shaft, and applying axial tension on a proximal portion of the suture to close the knotted loop against the distal end of the shaft.

27. A method as in claim 20 wherein the surgical needle is retained on the shaft while the shaft is introduced.

28. A method as in claim 27 wherein a slidable sleeve is disposed about a distal portion of the shaft such that the shaft may be introduced with the needle and suture surrounded by the sleeve.

29. A method as in claim 20 wherein the surgical needle is passed through the tissue using a needle holder.

30. A method as in claim 20 wherein axial tension is applied on the proximal portion of the suture using a handle which is slidably attached to the shaft.

31. A method as in claim 20 wherein tension is applied to a distal portion of the suture using a needle holder.

* * * * *